United States Patent [19]

Heppler

[11] 4,349,338

[45] Sep. 14, 1982

[54] DAILY INJECTION SITE GUIDE ASSEMBLY

[76] Inventor: Fred A. Heppler, 3117 Falcon Ave., Medford, N.Y. 11763

[21] Appl. No.: 225,614

[22] Filed: Jan. 16, 1981

[51] Int. Cl.³ .................. G09B 23/28; G09F 7/12; A47B 81/00; A61B 19/02

[52] U.S. Cl. .................................. 434/262; 40/594; 40/611; 206/364; 206/459; 206/828; 211/60 R; 312/209; 312/234

[58] Field of Search ............... 434/262, 265, 267, 272, 434/275, 428, 429, 238; 40/594, 611; 206/364, 365, 366, 370, 438, 459, 534, 828; 211/13, 60 R; 312/209, 234, 234.1, 234.5

[56] References Cited

U.S. PATENT DOCUMENTS

| 42,943 | 5/1864 | Hance | 312/209 X |
|---|---|---|---|
| 59,086 | 10/1866 | Skinner | 312/209 |
| 2,929,510 | 3/1960 | Penn | 211/60 R |
| 3,058,584 | 10/1962 | Marshall | 206/365 X |
| 3,348,894 | 10/1967 | Deberry | 312/209 |
| 3,704,529 | 12/1972 | Cioppa | 434/272 |
| 4,015,352 | 4/1977 | Prange | 40/594 |
| 4,039,080 | 8/1977 | Cappuccilli | 206/534 |
| 4,254,871 | 3/1981 | Poore | 206/534 |

Primary Examiner—William H. Grieb
Attorney, Agent, or Firm—Leonard W. Suroff

[57] ABSTRACT

An injection site guide assembly for storing and dispensing of disposable syringes and alcohol wipes or swabs comprising a housing having an upper end and spaced apart lower end with a holding assembly extending into the housing at the upper end so as to permit the storing of a plurality of the syringes therein and the syringes are adapted to be individually removed as required for use thereof. A cover is provided and adapted to be removably secured to the housing at the upper end for hygienically enclosing the holding assembly, with a mounting unit operatively associated with the housing so as to permit securement of the assembly on a wall or the like. An indicating assembly is used on the housing for illustrating various injection sites on the human body for controlled use of the syringes contained therein, with a retaining assembly extending on or into the housing to accept disposable wipes or the like for use in conjunction with the disposable syringes, and a container assembly removably secured to the housing at the lower end thereof.

32 Claims, 7 Drawing Figures

DAILY INJECTION SITE GUIDE ASSEMBLY

BACKGROUND OF THE INVENTION

The present invention relates to an injection site guide assembly that aids the user in dispensing medication from a syringe or the like. The syringe may be used in conjunction with wipes, swabs or the like, all of which may be disposable.

There is an increasing amount of people both in and outside of the United States that have diabetes or other illness for which daily injections of insulin or other medication is required. The inventor has found that when a person has to administer injections daily that unless a system is implemented that aids the user in varying the injection site daily, the person can easily forget which site on his or her body was used last. Site rotation is important to prevent one or more locations to become the prime areas of usage because of habit, convenience or location. The overuse of a particular site can cause tenderness as well as other possible medical problems.

The inventor has found that in addition to guiding the user as to the body site of use, it is most important to be able to store for easy dispensing a supply of syringes for one or more weeks at a time. To protect the diabetic or user as to proper rotation of the body injection sites, the inventor has found that an assembly of the present invention will substantially aid the user in this respect.

Although the invention will be particularly discussed as to use for a diabetic and the medication being insulin, it will be appreciated that it may be used by any person required to administer themselves or have administered to them by injection medication for any disease, syndrome or for other reason. In addition although the invention is illustrated for daily use it is also not to be limited to that singly, but any schedule which may be twice daily, etc.

OBJECTS OF THE INVENTION

An object of the invention is to provide an injection site guide assembly that permits the user to store a plurality of disposable syringes for insulin or other medication and use same in a plurality of body sites that are indicated on the assembly.

Another object of the invention is to provide for easy storage and disposal of syringes and alcohol wipes in an assembly that may be wall mounted and designed to provide the user with a daily schedule of injection sites on the human body.

Another object of the invention is to provide an injection site guide assembly that has a calendar thereon for aid in site selection.

Another object of the invention is to provide a high degree of hygiene or cleanliness for the syringes by completely incasing them from the time they are installed until the time they are dispensed or used.

Another object of the invention is to provide an injection site reminder on an as used real time basis that is superior to the prior state of the art devices.

Another object of the invention is to centerally locate all the necessary medical apparatus with guide for on site, and site of administration of injection, with disposal means for used apparatus, all in one convenient package or assembly.

Other objects and advantages of the invention will become apparent as the disclosure proceeds.

SUMMARY OF THE INVENTION

An injection site guide assembly is disclosed for storing and dispensing of syringes so as to permit an orderly use of the syringes by the user on a preselected routine. The assembly includes a housing means having an upper end and spaced apart lower end, with holding means extending into the housing means at the upper end so as to permit the storing of a plurality of the syringes therein and the syringes are adapted to be individually removed as required for use thereof. There is provided cover means adapted to be removably secured to the housing means at the upper end for enclosing the holding means.

Mounting means is operatively associated with the housing means so as to permit securement of the assembly on a wall or the like. This permits mounting of the housing means in the bathroom, such as in the closet, or other room convenient for the user. Indicating means on the housing for illustrating various injection sites on the human body for use of the syringes is provided. Container means is provided and is removably secured to the housing means at the lower end thereof. Retaining means extending on or into the housing means to accept disposable wipes or the like for use in conjunction with the syringes is also provided. The housing means includes a front and rear panel extending intermediate the ends, and a pair of side panels extending on opposite side of the front and rear panels. The holding means includes a plurality of equally spaced apart apertures extending downwardly from the upper end into the housing means. The cover means may include a rim extending circumferentially thereon, with the rim mating with the upper end of the housing means. The cover means may include a front wall and a rear wall, with a pair of side walls extending on opposite sides of the front and the rear walls, as well as a top wall joining all of the walls together at one end thereof, and the rim joining all of the walls together at the opposite end thereof. The cover means is used to enclose the upper end of the syringes and may include a lip extending downwardly from the rim at the front wall for extending into or partially overlapping relationship with the front panel of the housing means. The mounting means is contained on the rear panel and may include an adhesive or magnetic member or can be made or left free standing if so desired.

The indicating means includes a plurality of outlines of the human body, with an arrow pointing to the appropriate site of the body that is to receive an injection on a particular day. There are generally ten sites recommended for use, and seven are generally selected by the user. Each one of the selected seven out of ten outlines of the human body is in substantial alignment with a respective one of the plurity of the syringes in the holding means starting from left to right. The indicating means includes a plurality of ten self adhesive labels, seven to be selected and secured to the housing means by the user of the assembly applied from left to right if desired. The labels contain the human body outline and indicia means in the form of alpha abbreviations which coincide with the site of the body that the indicating arrow points to. There may also be provided alignment means to aid in positioning the indicating means onto the housing means. The indicating means may be shipped separately with the assembly and the user placing the self adhesive labels on the housing means himself or herself as indicated above. If desired the indicating means may be provided on the housing means prior to shipment to the end user.

To aid the user in the operation or use of the assembly there may be provided sequence means supplied with and adapted to be secured to the housing means. The seqence means includes at least one self adhering label having the respective days of the week thereon. The sequence means can include seven self adhearing labels, each label having a different day of the week thereon and labels may be applied by the user of the assembly starting with the day and ending on the day of the user's preferance. The sequence means is also applied in a normal manner starting from left to right.

The container means may also include a drawer having a cavity therein for disposal of syringes and wipes. To aid in utilization of the assembly there may be provided hinge means extending between the container means and the housing means so as to permit removal of the drawer away from the housing means such that the used syringes and wipes may be readily removed therefrom and the drawer slid back in place. In accordance with one embodiment of the invention the hinge means includes a pair of channels extending horizontally on the housing means adjacent to the lower end thereof, and a lip on each side of the container means. Each lip extending in one of the channels and being supported thereby. The channels on the housing means each include a horizontal flange, a first inwardly inclined bevel, an outwardly extending bevel coupled at one end to the first inwardly inclined bevel, and a second inwardly inclined bevel coupled at one end to the outwardly extending bevel. The lips on the container each include a horizontal edge, and a first inwardly inclined edge, an outwardly extending edge and a second inwardly inclined edge respectively connected to each other and mating with the bevels of the channel.

The retaining means includes a horizontally extending slot to accept the disposable wipes or the like therein and slopes rearwardly and downwardly into the housing means. The assembly may further include an adapter means securable to the housing means on one side thereof for the storage of insulin, and alcohol. The adapter means may include chamber means for the storage of containers of insulin or the like, with fluid reservoir means below the chamber means, as well as connecting means extending between the chamber means and the reservoir means to permit the flow of alcohol or the like into the reservoir means, and valve means at the lower end of the reservoir means to permit a controlled flow from the reservoir means through the valve means as desired, onto a cotton swab, or the like.

There is also provided coupling means to secure the adapter means to the housing means and closure means to cover the adapter means. In addition there may be provided joining means to secure the closure means to the adapter means.

In accordance with one embodiment of the invention the holding means shown includes a plurality of rows retaining the syringes. For example three of the rows are provided and each row can store seven syringes for a total of a three week supply, if one syringe is used daily, or a one week supply if three syringes are used daily.

In accordance with one embodiment of the invention by using this plurality of indica in each column perpendicular to each syringe allows for use of the assembly even by a child or person who may not be able to read or interpret the body site alpha abbreviations. Such person it is reasoned could easily follow the body sketches on symbols with body site indicating arrow, pictured in each column located on the front face of the housing means. The day of the week and body site indica could also be arranged in braille perpendicular to row of syringes to allow this invention to be utilized by a blind person.

The assembly may also be used as a traveling kit for the diabetic or user, as it conveniently contains all the medical apparatus necessary for administration of injections maintaining cleanliness and the same control, while traveling as well as at home.

BRIEF DESCRIPTION OF THE DRAWINGS

Although the characteristic features of this invention will be particularly pointed out in the claims, the invention itself, and the manner in which it may be made and used, may be beter understood by referring to the following description taken in connection with the accompanying drawings forming a part thereof, wherein like reference numerals refer to like parts throughout the several views and in which:

DETAILED DESCRIPTION OF THE DRAWINGS

Figure 1:
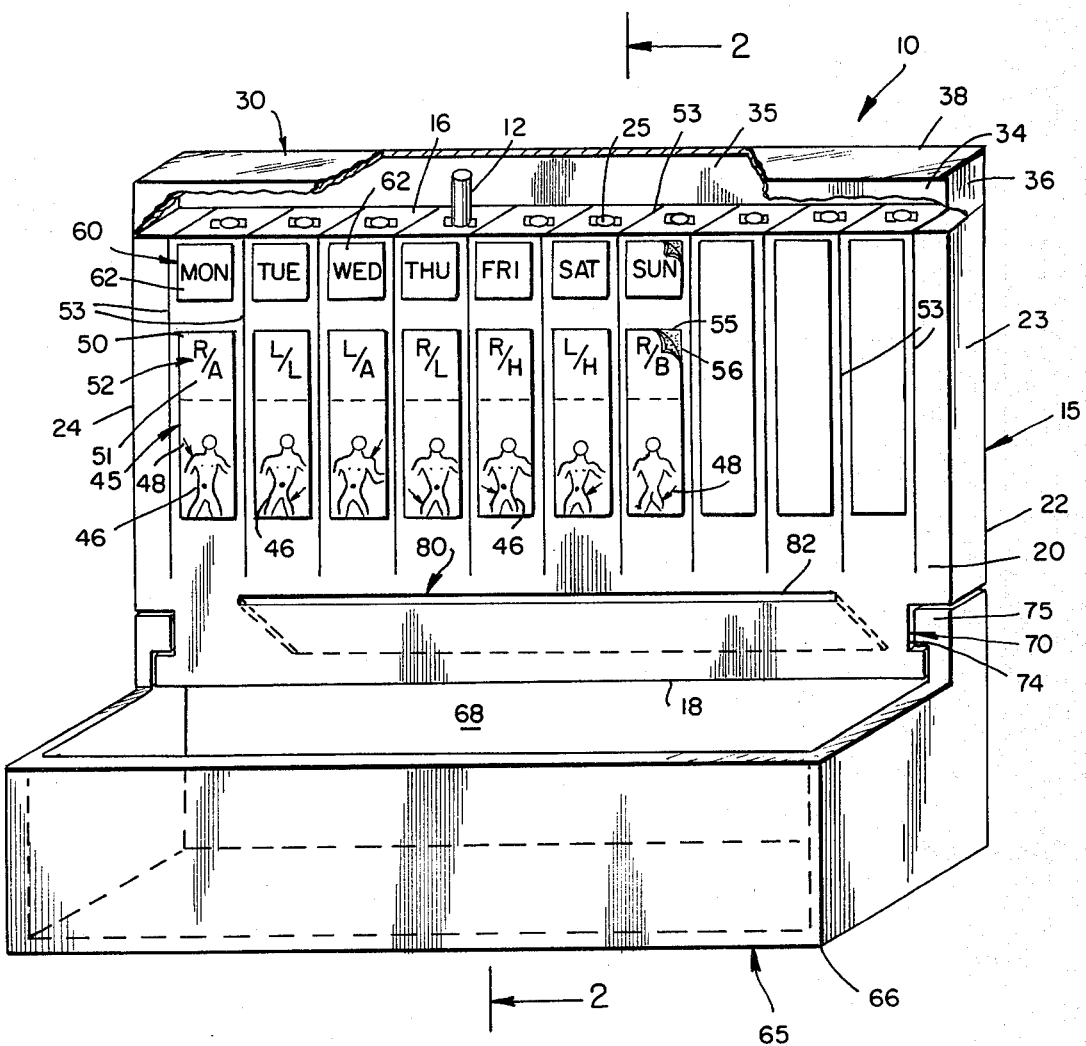
FIG. 1 is a perspective view, partly in section of an injection site guide assembly in accordance with the present invention.
Figure 2:
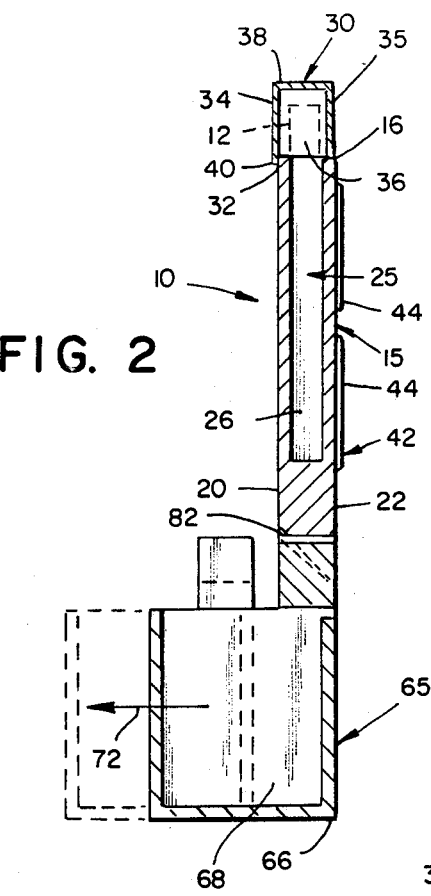
FIG. 2 is a cross-sectional view taken along lines 2—2 of FIG. 1.
Figure 5:
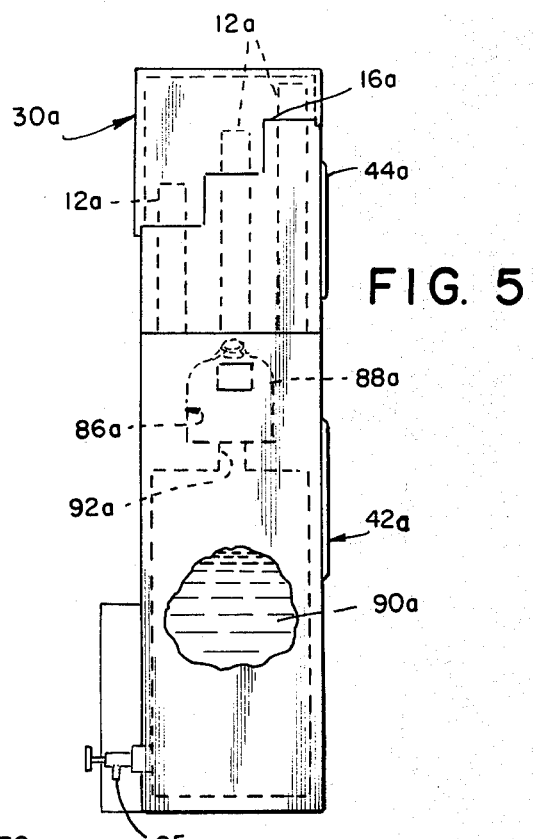
FIG. 5 is a side plan view of the assembly illustrated in FIG. 3.
Figure 4:
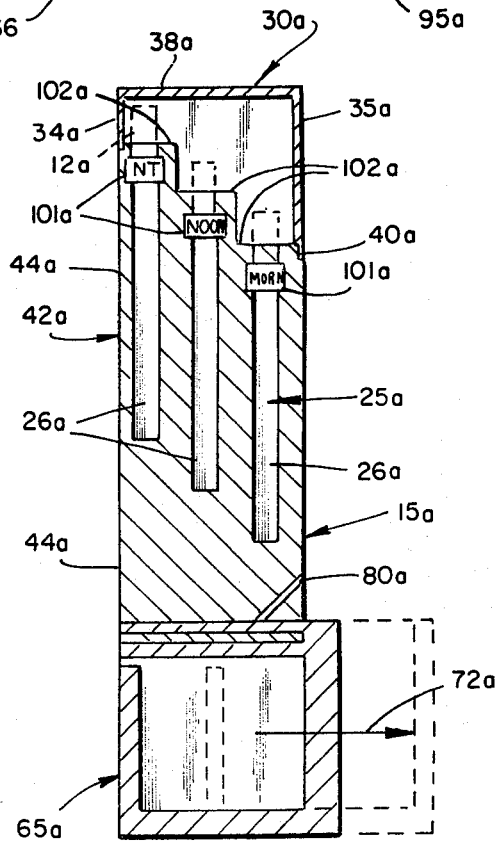
FIG. 4 is a cross-sectional view taken along the line 4—4 in FIG. 3.
Figure 3:
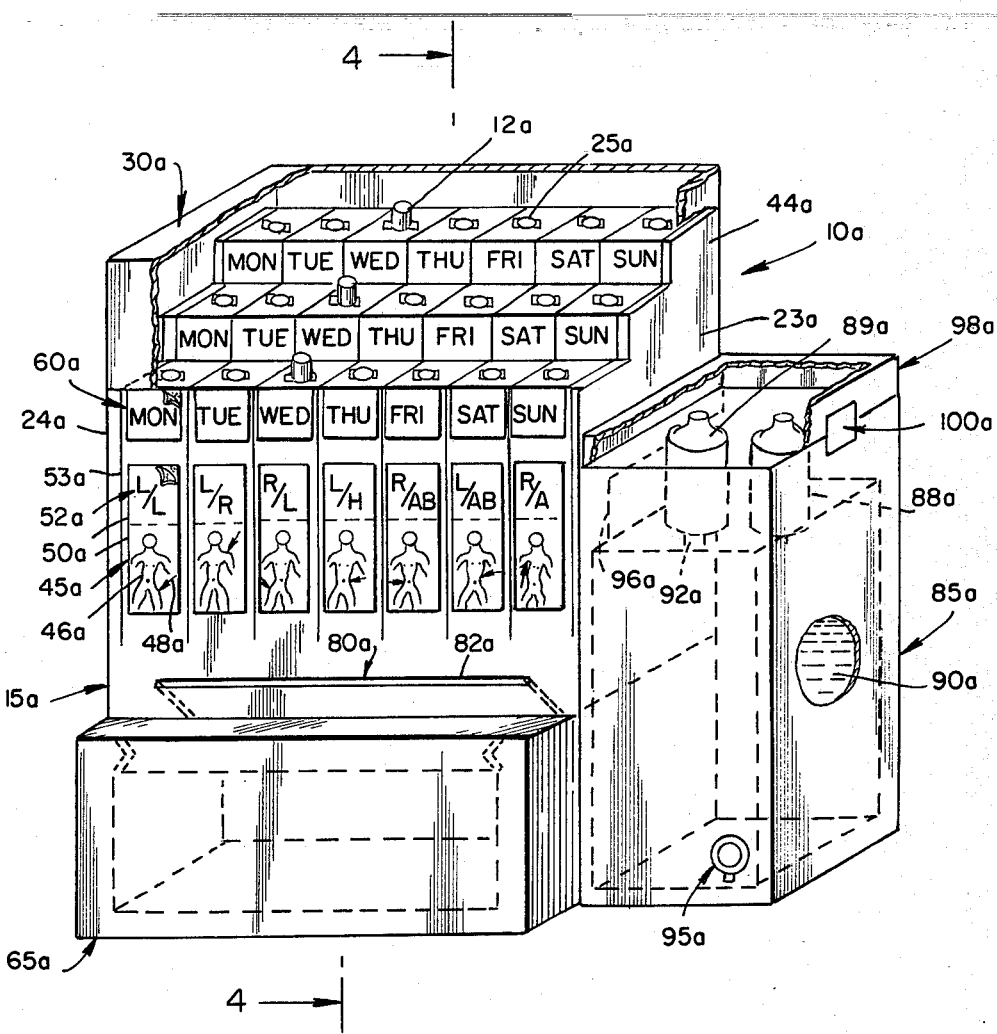
FIG. 3 is a perspective view, partly in section, of another embodiment of the present invention.
Figure 6:
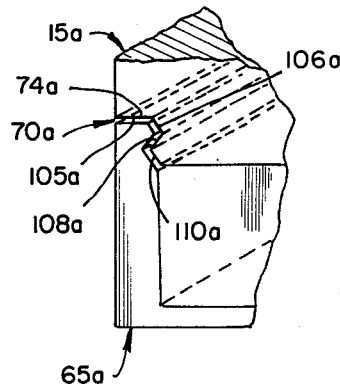
FIG. 6 is a fragmentary enlarged view of the hinge means associated with the container.
Figure 7:
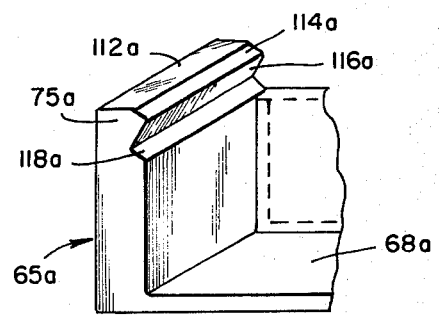
FIG. 7 is a fragmentary view similar to that illustrated in FIG. 6 of the container means.

Referring to the drawings there is illustrated in FIGS. 1 and 2, an injection site guide assembly 10 for storing and dispensing the contents of syringes 12 so as to permit an orderly use of the syringes 12 by the user or other person, on a preselected routine. The assembly 10 includes a housing means 15 having an upper end 16 and spaced apart lower end 18. The housing means includes a front panel 20 and rear panel 22 extending intermediate the ends 16 and 18. A pair of side panels 23 and 24 are on opposite sides of the front panel 20 and rear panel 22. The housing means 15 may be fabricated from a styrofoam plastic or other suitable plastic, wood, paper, metal or combination of these or other suitable construction materials. The finish would be smooth to touch with no sharp edges, and the color is optional.

Syringe holding means 25 extends into the housing means 15 at the upper end 16 so as to permit the storing of a plurality of the syringes 12 therein and the syringes 12 are adapted to be individually removed as required for use thereof. The holding means 25 includes a plurality of spaced apart apertures 26, which may be equally spaced apart, and extending downwardly from the upper end 16 into the housing means 15.

There is provided cover means 30 adapted to be removably secured to the housing means 15 at the upper end 16 for enclosing the holding means 25. The cover means 30 may include a rim 32 extending circumferentially thereon, with the rim 32 mating with the upper end 16 of the housing means 15. The cover means 30, may be rectangular in shape and may include a front wall 34 and a rear wall 35, with a pair of side walls 36 extending on opposite sides of the front wall 34 and the rear wall 35. A top wall 38 joins all of the walls 34, 35 and 36, together at one end thereof, and the rim 32 extends from the wall 34. The cover means 30 is used to enclose the upper end 16 of the housing means 15 and the syringes 12, and a lip 40 extends downwardly from the rim 32 at the front wall 34 for extending into or partially overlapping relationship with the front panel 20 of the housing means 15. The walls 34, 35, and 36 of cover walls 30, may also extend into a channel circumferentially around housing means 15 and adjoining walls 20, 22 23 and 24 of upper end 16.

Mounting means 42 is operatively associated with the housing means 15 so as to permit securement of the assembly 10 on a wall or the like. This permits mounting of the housing means 15 in the bathroom or other room convenient for the user. This mounting means 42 may be contained on the rear panel 22 and may include adhesive or magnetic strip members 44.

Indicating means 45, which may be in the form of self adhering labels, is provided on the housing means 15 for illustrating various injection sites on the human body for use of the syringes 12. The indicating means 45 includes a plurality of outlines 46 of the human body, with an arrow 48 pointing to the appropiate site of the body that is to receive an injection on a particular day. Each one of the plurality of outlines 46 of the human body is in substantial alignment with a respective one of the syringes 12 in the holding means 25. The indicating means 45 also includes a plurality of adhesive labels 50 adapted to be secured to the housing means 15 on the front panel 20, by the user of the assembly 10. The labels 50 contain the human body outline 46 and indicia means 52 in the form of alpha abbreviations 51 which coincide with the site of the body 46 that the indicating arrow 48 points to. Accordingly alpha abbreviation 51, R/A may stand for right arm, etc. There may also be provided alignment means 55 to aid in positioning the indicating means 45 onto the housing means 15. The indicating means 45 may be shipped separately with the assembly 10 and the user placing it on the housing means 15 on front panel 20. The alignment means 55 may include a line or lines 56 to aid in locating the labels 50. To aid the user vertical lines 53 are provided that are equally spaced between the holes 25 on the front panel 20 and also equally spaced and parallel to each other as shown on end 16.

To aid the user in the operation or use of the assembly 10 there may be provided sequence means 60 adapted to be secured to the housing means 15 on the front panel 20. The sequence means 60 includes at least one self adhering label or member 62 having the respective days of the week thereon. The sequence 60 can include seven self adhering labels, each label 62 having a different day of the week thereon and labels 62 may be applied by the user of the assembly 10 starting one day and ending on the day of the user's preferance.

Container means 65 is provided and is removably secured to the housing means 15 at the lower end 18 thereof. The container means 65 may also include a drawer 66 having a cavity 68 therein for disposal of syringes or other items. To aid in utilization of the assembly 10 there may be provided hinge means 70 extending between the container means 65 and the housing means 15 so as to permit removal of the drawer 66 away from the housing means 15, as illustrated by arrow 72 in FIG. 2, such that the used syringes may be readily removed therefrom and the drawer 66 slid back in place. The hinge means 70 includes a pair of channels 74 extending horizontally on the housing means 15 adjacent to the lower end 18 thereof, and a lip 75 on each side of the container means 65. Each lip 75 extending in one of the channels 74 and being supported thereby and sliding therein.

Retaining means 80 extending on or into the housing means 15 to accept disposable wipes or the like for use in conjunction with the syringes is also provided. Retaining means 80 is provided and includes a horizontally extending slot 82 to accept the disposable wipes or the like in a stored position therein and slopes rearwardly and downwardly into the housing means 15. Accordingly the assembly 10 as illustrated in FIGS. 1 and 2 provides for the diabetic or user all of the necessary conveniences to tailor the assembly 10 to his or her particular needs. The sequence means 60 and indicating means 45, may be shipped separately with the housing means 15 and the user placing same in place as to his or her preference.

The invention provides convenience for the person taking medication, such as insulin, by an injection on a daily basis. The user can now view the indicating means 45 associated with a particular day of the sequence means 60 and see the location for the injection. FIG. 1 shows that more than seven syringes 12 may be stored in the holding means 25, and any unselected syringes 12 in the holding means 25 to the right of the seven selected may be considered spares.

FIGS. 3 through 7 illustrate another embodiment of the invention in which the assembly 10a includes all of the basic features of the embodiment in FIGS. 1 and 2 and further provides for adapter means 85a securable to the housing means 15a on one side 23a thereof for the storage of insulin, alcohol or the like. The adapter means 85a may include chamber means 86a for the storage of containers 88a of insulin or the like. Fluid reservoir means 90a extends below the chamber means 86a with connecting means 92a extending between the chamber means 86a and the reservoir means 90a to permit the flow of alcohol or the like into the reservoir means 90a. Valve means 95a is located at the lower end of the reservoir means 90a to permit a controlled flow from the reservoir means 90a through the valve means 95a as desired.

There is also provided coupling means 96a to secure the adapter means 85a to the housing means 15a and closure means 98a to cover the adapter means 85a. In addition there may be provided joining means 100a to secure the closure means 98a to the adapter means 85a. The coupling means 96a may be an adhesive to permanently bond the adapter means 85a to the housing means 15a. If desired they may be fabricated as one unit. The coupling means 100a may be a hinge or the like to permit the closure means 98a to be opened when access to the chamber means 86a is desired. The adapter means 85a permits the user to retain a supply of alcohol and dispense same through the valve means 95a as desired. The containers 88a and 89a may be insulin of one or two types depending on the user's needs.

In accordance with the embodiment of the invention in FIGS. 3 through 7 the holding means 25a includes a plurality of rows 102a retaining the syringes 12a. For example three of the rows 102a are provided and each row can store seven syringes for a total of a three week supply for a person who uses one syringe daily. The rows 102a are at the upper end 16a of the housing means 15a and may be in steps to visually aid the user. In addition self adhering labels 101a may also be supplied blank on means 15a to be marked by user as to time of day i.e. MOR, NOON, NT, and aligned in that row 102a indicating when that syringe 12a may have to be administered. The channels 74a on the housing means 15a forming the hinge means 70a, each include a horizontal flange 105a, a first inwardly inclined bevel 106a, and outwardly extending bevel 108a coupled at one end to the first inwardly inclined bevel 106a, and a second inwardly inclined bevel 110a coupled at one end to the outwardly extending bevel 108a. The lip 75a on the container means 65a each include a horizontal edge 112a, and a first inwardly inclined edge 114a, an outwardly extending edge 116a and a second inwardly inclined edge 118a respectively connected to each other and mating with the bevels 105a, 106a, 108a and 110a on the channel 74a. This arrangement provides for a convenient movement in the opening and closing of the container means 65a.

The assembly 10a also provides for the retaining means 80a for disposable wipes or the like. The user is provided with the comfort that he or she may rely on the assembly 10a to have and hold all the necessary medical apparatus for injection and a daily aid to body site to be administered for better control. After a period of time, of one to three weeks the assembly 10a is resupplied for continuous use over and over again.

Although illustrative embodiments of the invention have been described in detail herein with reference to the accompanying drawings, it is to be understood that the invention is not limited to the preceise embodiments, and that various changes and modifications may be effected therein without departing from the scope or spirit of the invention.

I claim:

1. An injection site guide assembly for storing and dispensing of disposable syringes comprising in combination:
   A. housing means having an upper end and spaced apart lower end,
   B. holding means extending into said housing means at said upper end so as to permit the storing of a plurality of the syringes therein and the syringes are adapted to be individually removed as required for use thereof,
   C. cover means adapted to be removably secured to said housing means at said upper end for enclosing said holding means,
   D. indicating means on said housing means for illustrating various injection sites on the human body for use of the syringes,
   E. retaining means associated with said housing means to accept disposable wipes or the like for use in conjunction with the syringes, and
   F. container means removably secured to said housing means at said lower end thereof.

2. An assembly as defined in claim 1, wherein said housing means includes:
   a. a front and rear panel extending intermediate said ends, and
   b. a pair of side panels extending on opposite side of said front and rear panels.

3. An assembly as defined in claim 2, wherein said holding means includes a plurality of spaced apart apertures extending downwardly from said upper end into said housing means.

4. An assembly as defined in claim 2, wherein said cover means includes a rim extending circumferentially thereon, said rim mating with said upper end of said housing means.

5. An assembly as defined in claim 4, wherein said cover means includes:
   a. a front wall and a rear wall,
   b. a pair of side walls extending on opposite sides of said front and said rear walls,
   c. a top wall joining all of said walls together at one end thereof, and
   d. said rim joining all of said walls together at the opposite end thereof.

6. An assembly as defined in claim 5, said cover means further including a lip extending downwardly from said rim on at least said front wall for extending into overlapping or interlocking relationship with said housing means.

7. An assembly as defined in claim 2, and further including mounting means associated with said housing means so as to permit positionment of the assembly on a surface.

8. An assembly as defined in claim 7, wherein said mounting means includes an adhesive member or the like on said rear panel.

9. An assembly as defined in claim 1, wherein said indicating means includes a plurality of outlines of the human body, with an arrow pointing to the appropriate site of the body that is to receive an injection on a particular day.

10. An assembly as defined in claim 9, wherein each one of said plurality of outlines of the human body is in substantial alignment with a respective one of said plurality of the syringes, in said holding means.

11. An assembly as defined in claim 10, wherein said indicating means includes a plurality of labels adapted to be secured to said housing means by the user of the assembly.

12. An assembly as defined in claim 11, wherein said labels each include indicia means in the form of alpha abbreviations which coincide with the site of the body that said arrow points to.

13. An assembly as defined in claim 1, and further including alignment means to aid in positioning said indicating means onto said housing means.

14. An assembly as defined in claim 1, and further including sequence means adapted to be secured to said housing means.

15. An assembly as defined in claim 14, wherein said sequence means include at least one label having the respective days of the week thereon and said label is self adhering.

16. An assembly as defined in claim 15, wherein said sequence means includes seven labels, each said label having a different day of the week thereon and said labels may be applied by the user of the assembly starting and ending on the day of the user's preferance.

17. An assembly as defined in claim 1, wherein said container means includes a drawer having a cavity therein for disposal of syringes, wipes or swabs.

18. An assembly as defined in claim 17, and further including hinge means extending between said container means and said housing means so as to permit removal of said drawer away from said housing means such that the syringes and wipes may be readily removed therefrom and the drawer slid back in place.

19. An assembly as defined in claim 18, wherein said hinge means includes:
  a. a pair of channels extending horizontally on said housing means adjacent to said lower end thereof, and
  b. a lip on each side of said container means, each said lip extending in one of said channels and being supported thereby.

20. An assembly as defined in claim 19, wherein said channels on said housing means each include:
  a. a horizontal flange,
  b. a first inwardly inclined bevel,
  c. an outwardly extending bevel coupled at one end to said first inwardly inclined bevel, and
  d. a second inwardly inclined bevel coupled at one end to said outwardly extending bevel.

21. An assembly as defined in claim 20, wherein said lips on said container each include:
  a. a horizontal edge, and
  b. a first inwardly inclined edge, an outwardly extending edge and a second inwardly inclined edge respectively connected to each other and mating with said bevels of said channel.

22. An assembly as defined in claim 1, wherein:
  a. said housing means includes a front panel and rear panel extending intermediate said ends,
  b. said mounting means extends on said rear panel, and
  c. said indicating means, and said retainer means are associated with said front panel.

23. An assembly as defined in claim 22, wherein said indicating means extends on or above said retaining means.

24. An assembly as defined in claim 1, wherein said retaining means includes a horizontally extending slot to accept said disposable wipes or the like therein.

25. An assembly as defined in claim 24, wherein said slot slopes rearwardly and downwardly into said housing means.

26. An assembly as defined in claim 1, and further including adapter means securable to said housing means on one side thereof for the storage of insulin, alcohol or the like.

27. An assembly as defined in claim 26, said adapter means including:
  a. chamber means for the storage of containers of insulin or the like,
  b. fluid reservoir means below said chamber means,
  c. connecting means extending between said chamber means and said reservoir means to permit the flow of alcohol or the like into said reservoir means, and
  d. valve means at the lower end of said reservoir means to permit a controlled flow from said reservoir means through said valve means as desired.

28. An assembly as defined in claim 27, and further including coupling means to secure said adapter means to said housing means.

29. An assembly as defined in claim 27, and further including closure means to cover said adapter means.

30. An assembly as defined in claim 29, and further including joining means to secure said closure means to said adapter means.

31. An assembly as defined in claim 1, wherein said holding means includes a plurality of rows for retaining said syringes.

32. An assembly as defined in claim 31, wherein each said row can store seven or more syringes.

* * * * *